(12) United States Patent
Hur et al.

(10) Patent No.: US 11,285,307 B2
(45) Date of Patent: Mar. 29, 2022

(54) DRUG DELIVERY INTEGRATED CIRCUIT (IC) AND SYSTEM

(71) Applicant: University of Florida Research Foundation, Incorporated, Gainesville, FL (US)

(72) Inventors: Byul Hur, College Station, TX (US); John Hardy, Lancaster (GB); William R. Eisenstadt, Gainesville, FL (US); Christine E. Schmidt, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 849 days.

(21) Appl. No.: 15/999,657

(22) PCT Filed: Feb. 17, 2017

(86) PCT No.: PCT/US2017/018386
§ 371 (c)(1),
(2) Date: Aug. 20, 2018

(87) PCT Pub. No.: WO2017/143200
PCT Pub. Date: Aug. 24, 2017

(65) Prior Publication Data
US 2020/0215317 A1    Jul. 9, 2020

Related U.S. Application Data

(60) Provisional application No. 62/297,383, filed on Feb. 19, 2016.

(51) Int. Cl.
*A61M 37/00*        (2006.01)
*A61M 5/142*        (2006.01)
(Continued)

(52) U.S. Cl.
CPC ........... *A61M 37/00* (2013.01); *A61B 5/4839* (2013.01); *A61K 9/0009* (2013.01);
(Continued)

(58) Field of Classification Search
CPC ..................... A61K 9/0097; A61M 2205/0244
See application file for complete search history.

(56) References Cited

U.S. PATENT DOCUMENTS 6,571,125 B2   5/2003   Thompson
7,226,442 B2   6/2007   Sheppard, Jr. et al.
(Continued)

FOREIGN PATENT DOCUMENTS

WO    WO-0135928 A1 *   5/2001   ............... A61F 2/91
WO    WO-0141736 A2 *   6/2001   ........... A61K 9/0009
(Continued)

OTHER PUBLICATIONS

Hur et al., "Low-Power Wireless Climate Monitoring System With RFID Security Access Feature for Mosquito and Pathogen Research," IEEE 2015 First Conference on Mobile and Secure Services, Feb. 2015, pp. 1-5.
(Continued)

*Primary Examiner* — Jenna Zhang
(74) *Attorney, Agent, or Firm* — Alston & Bird LLP

(57) ABSTRACT

Wireless and non-wireless drug delivery integrated circuits, systems, and methods of delivering therapeutic pharmaceutical compounds are provided. The system can include a control module, a wireless drug delivery integrated circuit, a first electrode and a second electrode that are both attached to the wireless drug delivery integrated circuit, an electroactive polymer, and a pharmaceutical compound. The electroactive polymer and the pharmaceutical compound can be formed as films on one of the electrodes and, when placed in a solution, a voltage potential can be applied across the
(Continued)

electrodes causing the pharmaceutical compound to be released into the solution.

18 Claims, 8 Drawing Sheets

(51) Int. Cl.
  *G16H 40/67*   (2018.01)
  *A61M 31/00*   (2006.01)
  *A61K 9/00*   (2006.01)
  *A61B 5/00*   (2006.01)

(52) U.S. Cl.
  CPC ........... *A61K 9/0097* (2013.01); *A61M 5/142* (2013.01); *A61M 31/002* (2013.01); *G16H 40/67* (2018.01); *A61M 2205/0244* (2013.01); *A61M 2205/0283* (2013.01); *A61M 2205/3368* (2013.01); *A61M 2205/3523* (2013.01); *A61M 2205/502* (2013.01); *A61M 2205/8206* (2013.01); *A61M 2205/8237* (2013.01)

(56) References Cited

U.S. PATENT DOCUMENTS

| | | | |
|---|---|---|---|
| 7,981,106 B2 | 7/2011 | Gilad | |
| 2006/0015058 A1* | 1/2006 | Kellogg | A61B 5/14514 604/22 |
| 2008/0083041 A1* | 4/2008 | Santini | A61B 1/041 800/9 |
| 2008/0228044 A1* | 9/2008 | Kurt | A61B 5/14532 600/300 |
| 2011/0202032 A1* | 8/2011 | Shih | A61M 5/14276 604/500 |
| 2015/0265712 A1* | 9/2015 | Hardy | A61K 31/00 604/20 |

FOREIGN PATENT DOCUMENTS

| | | |
|---|---|---|
| WO | WO 2007/129240 A1 | 11/2007 |
| WO | WO 2011/014887 A1 | 2/2011 |

OTHER PUBLICATIONS

Hur et al., "Progress in Development of the Low-Power Wireless Multiple Temperature Sensor Pole for Pesticide, Agriculture, and Mosquito Research," Proceedings of the IEEE Southeast Con 2015, Apr. 2015, pp. 1-6.

Svirskis et al., "Electrochemically Controlled Drug Delivery Based on Intrinsically Conducting Polymers," *Journal of Controlled Release* 146, (2010) pp. 6-15.

Pillay et al., "A Review of Integrating Electroactive Polymers as Responsive Systems for Specialized Drug Delivery Applications," *Wiley Periodicals, Inc.*, Jul. 2013, pp. 2039-2054, [online], [retrieved from the Internet Apr. 30, 2019] <URL: https://onlinelibrary.wiley.com/doi/abs/10.1002/jbm.a.34869>.

Allen, Theresa M., et al., "Drug Delivery Systems: Entering the Mainstream," *Science*, Mar. 19, 2004, vol. 303, pp. 1818-1822, www.sciencemag.org.

Gao, Wen, et al., "Action at a distance: Functional Drug Delivery Using Electromagnetic-Field-Responsive Polypyrrole Nanowires," *Langmuir*, Jun. 9, 2014, pp. 7778-7788, vol. 30, No. 26, ACS Publications.

Gao, Wen, et al., "Remote-Controlled Eradication of Astrogliosis in Spinal Cord Injury via Electromagnetically-Induced Dexamethasone Release From "Smart" Nanowires," *Journal of Controlled Release*, 2015, pp. 22-27, vol. 211, Elsevier, B.V.

Hardy, J. G., et al., "Biodegradable electroactive polymers for electrochemically-triggered drug delivery," Journal of Materials Chemistry B, Aug. 19, 2014, pp. 6809-6822, vol. 2, No. 39, retrieved from <https://pure.qub.ac.uk/portal/files/12455080/101039C4TB00355A.pdf> on Aug. 10, 2018.

Hardy, John, et al., "Peptide-Directed Assembly of Functional Supramolecular Polymers for Biomedical Applications: Electroactive Molecular Tongue-Twisters (Oligoalanine-Oligoaniline-Oligoalanine) for Electrochemically Enhanced Drug Delivery," *Journal of Materials Chemistry B*, 2015, pp. 5005-5009,vol. 3, No. 25, retrieved from <http://pubs.rsc.org/en/content/getauthorversionpdf/C5TB00106D> on Aug. 10, 2018.

Iniernational Searching Authority, International Search Report and Written Opinion for International Application No. PCT/US2017/018386, dated May 22, 2017, 12 pages, Korean Intellectual Property Office, Korea.

Liechty, William, et al., "Polymers for Drug Delivery Systems," *Annual Review of Chemical and Biomolecular Engineering*, 2010, 29 pages, retrieved authors' manuscript from <https://www.ncbi.nlm.nih.gov/pmc/articles/PMC3438887/> on Aug. 10, 2018.

Sershen, S. R., et al., "Temperature-Sensitive Polymer-Nanoshell Composites for Photothermally Modulated Drug Delivery," *Journal of Biomedical Materials Research*, 2000, vol. 51, No. 3, pp. 293-298, retrieved from <http://westlab.pratt.duke.edu/sites/westlab.pratt.duke.edu/files/Temperature-sensitive%20polymer%E2%80%93nanoshell%20composites%20for%20photothermally%20modulated%20drug%20delivery.pdf> on Aug. 10, 2018.

\* cited by examiner

… (omitting running header "US 11,285,307 B2")

DRUG DELIVERY INTEGRATED CIRCUIT (IC) AND SYSTEM

CROSS REFERENCE TO RELATED APPLICATION

This application is a national stage application, filed under 35 U.S.C. § 371, of International Application No. PCT/US2017/018386, filed Feb. 17, 2017, which claims the benefit of U.S. Provisional Application Ser. No. 62/297,383, filed Feb. 19, 2016, the contents of both of which are hereby incorporated by reference in their entirety.

BACKGROUND OF INVENTION

Drug delivery refers to approaches, formulations, technologies, and systems for transporting a pharmaceutical compound in the body to safely achieve its desired therapeutic effect. It often involves scientific site-targeting within the body or facilitating systemic pharmacokinetics. In any case, it is typically concerned with both the quantity and duration of drug presence. Drug delivery is often approached via a drug's chemical formulation, but it may also involve medical devices or drug-device combination products. Drug delivery is a concept heavily integrated with dosage form and route of administration, the latter sometimes even being considered part of the definition.

Devices capable of the precise control of levels of drugs in specific tissues or the blood stream can enable maintenance of the drug within a therapeutic window (effective yet not associated with undesirable side effects). Many conditions, including Alzheimer's disease, cancer, cardiovascular diseases, diabetes, epilepsy, pain, Parkinson's disease, and infectious diseases can be treated most effectively by drugs with chronopharmacologies synchronized with the chronobiology of the specific condition.

Current efforts in the area of drug delivery include targeted delivery in which the drug is only active in the target area of the body (for example, in cancerous tissues) and sustained release formulations in which the drug is released over a period of time in a controlled manner from a formulation. Types of sustained release formulations include liposomes, drug-loaded biodegradable microspheres and drug-polymer conjugates. However, drawbacks of the related art include the need to be tethered to stationary equipment and constant human intervention to control the quantity, duration, and target site of drug delivery.

BRIEF SUMMARY

To address the above-mentioned problems, new equipment and methods are needed for drug delivery. The subject invention provides novel and advantageous drug delivery systems and methods.

In one embodiment, a drug delivery system includes a control module, a wireless drug delivery integrated circuit (WDDIC), a first electrode and a second electrode that are both attached to the wireless drug delivery integrated circuit, a first electroactive polymer, and a first pharmaceutical compound.

In another embodiment, a drug delivery method includes providing a wireless drug delivery integrated circuit, providing a control module suitable for controlling the wireless drug delivery integrated circuit, providing a first electrode and a second electrode that are both attached to the wireless drug delivery integrated circuit, providing a first electroactive polymer, providing a first pharmaceutical compound, and releasing the first pharmaceutical compound into a first solution by generating a first voltage difference between the first electrode and the second electrode.

In another embodiment, a drug delivery integrated circuit (DDIC) includes a first electrode and a second electrode that are both attached to the DDIC, a first electroactive polymer, and a first pharmaceutical compound. The DDIC is suitable for releasing the first pharmaceutical compound into a first solution by generating a first voltage difference between the first electrode and the second electrode, and the DDIC can be pre-programmed to begin drug release upon crossing a measurement threshold. The measurement threshold can include one or more of a temperature, sugar level, time, and a concentration. Other factors along these lines can be included in the measurement threshold.

DETAILED DISCLOSURE

Figure 1:
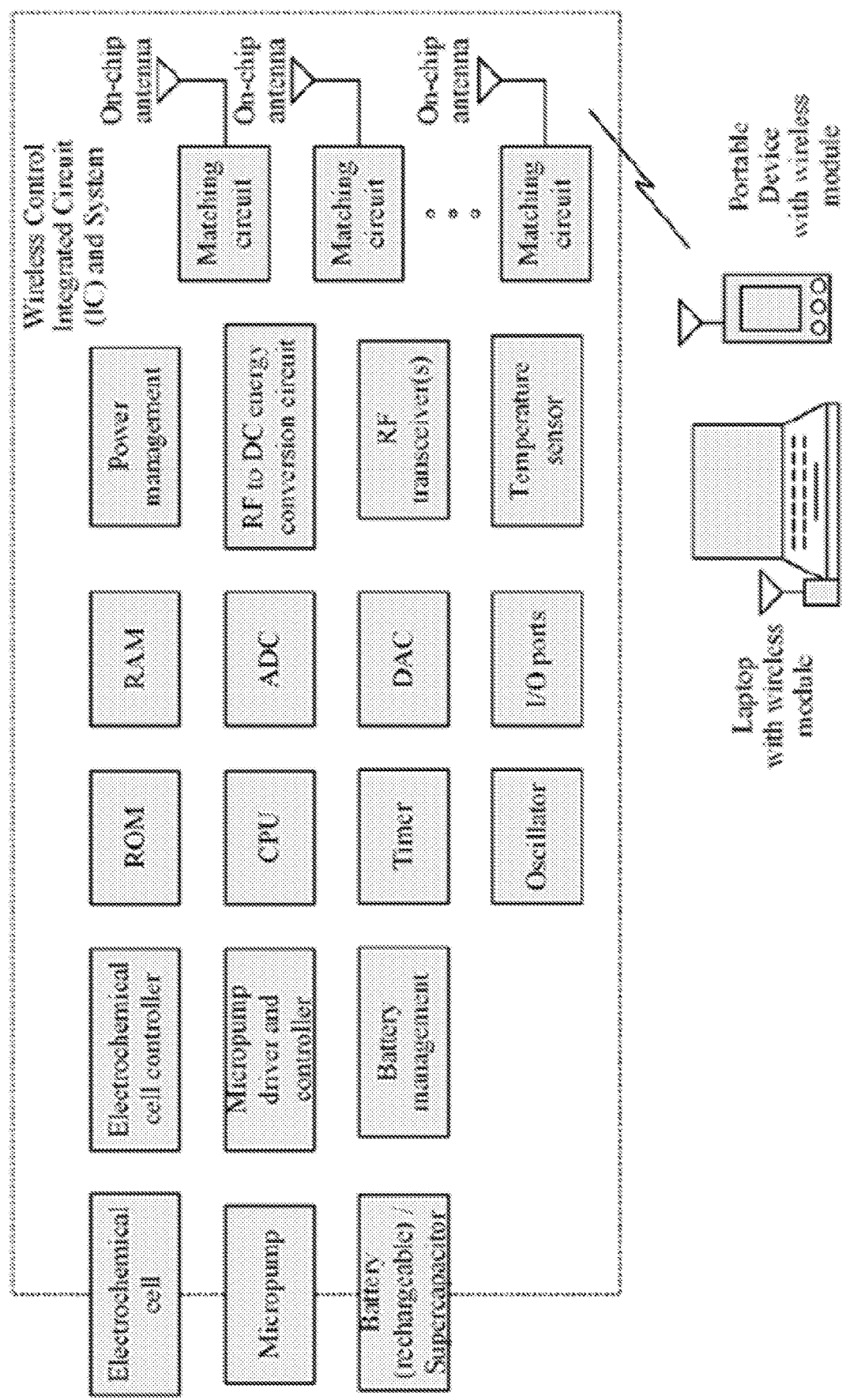
FIG. 1 is a block diagram of a wireless drug delivery integrated circuit (IC) system according to an embodiment of the present invention.

The subject invention provides novel and advantageous drug delivery methods, systems, and methods of using the systems. More specifically, the subject invention provides a drug delivery integrated circuit, system, and method of wirelessly delivering therapeutic pharmaceutical compounds.

A drug delivery system can include a control module, a wireless drug delivery integrated circuit (WDDIC), a first electrode and a second electrode that are both attached to the wireless drug delivery integrated circuit, a first electroactive polymer, and a first pharmaceutical compound. The first electroactive polymer and the first pharmaceutical compound can be layered in films on the first electrode. The drug delivery system can have multiple antennas that are suitable for supplying energy to the wireless drug delivery integrated circuit. The first electrode can be made of, for example, bioinert glassy carbon, and the second electrode can be made of, for example, platinum. Other non-limiting examples of electrode materials include steel, platinum, iridium oxide, gold, magnesium, tungsten, silicon, and platinum-iridium. The drug delivery system can further include a third electrode and a fourth electrode in a second chamber with a second pharmaceutical compound, wherein the first electrode and the second electrode are contained in a first chamber with the first pharmaceutical compound. The drug delivery system can also include an inlet, an outlet, and a micropump as a secondary method of drug delivery control.

A drug delivery method can include providing a WDDIC, providing a control module suitable for controlling the WDDIC, providing a first electrode and a second electrode, which are both attached to the WDDIC, providing a first electroactive polymer, providing a first pharmaceutical compound, and releasing the first pharmaceutical compound into a first solution by generating a first voltage difference between the first electrode and the second electrode. The drug delivery method can further include providing a third electrode and a fourth electrode and releasing a second pharmaceutical compound. The method can further include providing a first chamber that contains the first solution, the first electrode, and the second electrode and providing a first inlet, a first micropump, and a first outlet, wherein the release of the first pharmaceutical compound out of the first chamber uses the first inlet, the first micropump, and the first outlet. The first polymer can include, for example, oligoanilines linked to polycaprolactone (PCL, 2 kDa) via ester bonds, though embodiments are not limited thereto and other electroactive polymers can be used. The first electroactive polymer and the first pharmaceutical compound can be layered in films on the first electrode.

A non-wirelessly controlled embodiment of the present invention includes providing a drug delivery integrated circuit (DDIC), providing a first electrode and a second electrode that are both attached to the DDIC, providing a first electroactive polymer, providing a first pharmaceutical compound, and releasing the first pharmaceutical compound into a first solution by generating a first voltage difference between the first electrode and the second electrode. The DDIC can be pre-programmed to begin control of drug release upon crossing a measurement threshold, and the measurement threshold can include one or more of a temperature, sugar level, time, concentration, and so forth. The DDIC can also include one or more of the additional features discussed with regards to the WDDIC, such as more than two electrodes, more than one drug, more than one polymer, one or more chambers, one or more inlets/outlets, and/or a flow controller.

Drug delivery systems can use polymer-based materials to improve pharmacological and therapeutic properties. Polymers have been used as elements in drug delivery technology because they can control the release of therapeutic agents. Although there are many clinical implementation hurdles, intelligent drug delivery systems can bring innovation and change to the treatment of diseases. Stimuli-responsive drug delivery systems are particularly useful in the treatment of such conditions because they have potential for spatiotemporally controlled drug delivery. Materials responding to stimuli such as enzymes, light, pH, temperature, ultrasound, and electric/magnetic fields can be used as drug delivery devices. Biodegradable electroactive/conductive polymer-based materials for electrochemically triggering drug delivery can also be used. Examples of polymers that can be applied in the present invention include poly (fluorene)s, polyphenylenes, polypyrenes, polyazulenes, polynaphthalenes, poly(acetylene)s, poly(p-phenylene vinylene), poly(pyrrole)s, polycarbazoles, polyindoles, polyazepines, polyanilines, poly(thiophene)s, poly(3,4-ethylenedioxythiophene), and poly(p-phenylene sulfide).

The miniaturization and integration of wireless and non-wireless drug delivery systems is an essential step for practical use of drug delivery applications. In embodiments of the present invention, wireless drug delivery integrated circuits, systems, and methods of wirelessly delivering therapeutic pharmaceutical compounds are presented. In addition, non-wireless drug delivery integrated circuits, systems, and methods of delivering therapeutic pharmaceutical compounds are presented. Applications for this invention include, for example, implantable (e.g, in the bloodstream or at a site where delivery is desired) and non-implantable use (e.g., via an intravenous therapy bag) in humans and other animals.

FIG. 1 is a simplified block diagram of a wireless drug delivery integrated circuit (IC) and system according to an embodiment of the present invention. Referring to FIG. 1, the system includes a laptop acting as the control module and the wireless drug delivery integrated circuit (WDDIC). The WDDIC has various components including a power management unit, a temperature sensor, a CPU, radio frequency (RF) transceivers, an RF-to-DC energy conversion circuit, on-chip antennas, an electrochemical cell and its controller, a micropump and its controller, a battery/supercapacitor, read-only memory (ROM), random access memory (RAM), an analog to digital converter (ADC), a digital to analog converter (DAC), a timer, an oscillator, and I/O ports. Further, all of the components except for the electrochemical cell, micropump, and battery/supercapacitor can be integrated in a single circuit board.

The antennas can act solely as signal transmitters or can also be a source of power. The on-chip antennas can be stacked on the IC, or they can be fabricated using one of the RF layers of the IC. It is preferable that antennas be integrated in the chip and work at high frequency bands to miniaturize the system. If the antennas work at low frequency bands, they may be too large to integrate on the chip. If it is desired for the antennas to operate at a low frequency band, they can be implemented as off-chip components that are attached to or stacked on the IC. Ranges of frequency bands that could be applied in the present invention include 1 kHz-1 MHz, 10 kHz-1 GHz, 10 MHz-1 GHz, and 1 GHz-10 THz, and 3 Hz to 300 GHz. It should also be understood that different ranges of frequencies may be used for harvesting than for communication and more than one frequency band may be used for communication, energy harvesting, or both. One antenna may be used; however, multiple antennas can be used to increase energy harvesting efficiency. The RF-to-DC conversion varies by frequency, and the use of multiple frequency bands and multiple antennas can provide a better chance of good RF-to-DC conversion as there are many RF frequency standards that use various frequencies.

Even if only one RF frequency band is used for both the energy conversion and communication, multiple antennas can still help increase energy efficiency. If multiple antennas are used, a phased array antenna can be formed to increase performance. For instance, if there are three ambient frequency bands and three antennas (or antenna groups such as in phased array antennas), the RF-to-DC conversion can operate using all three frequencies, thereby increasing the likelihood of efficient RF-to-DC conversion. Modern wireless power transfer generally operates in low frequency bands, which require relatively large antennas. However, if the frequency bands are chosen properly, the use of multiple antennas using one or more frequency bands can be fabricated in a portable or even implantable size. As the drug delivery IC can have multiple antennas and transceivers, it can support multiple RF standards including Bluetooth, Bluetooth low energy, NFC, ANT and ANT+, Zigbee, WiFi, Cellular network including 2G, 3G, 4G, 5G, and satellite communication, as well as others.

A battery (one time use or rechargeable) or supercapacitor may be used to power the portable device. That is, if RF power is sufficient, a battery may not be necessary. Because it is not currently feasible to fully integrate the battery/supercapacitor on a chip, they can be fabricated separately and attached or stacked on the IC.

Figure 2:
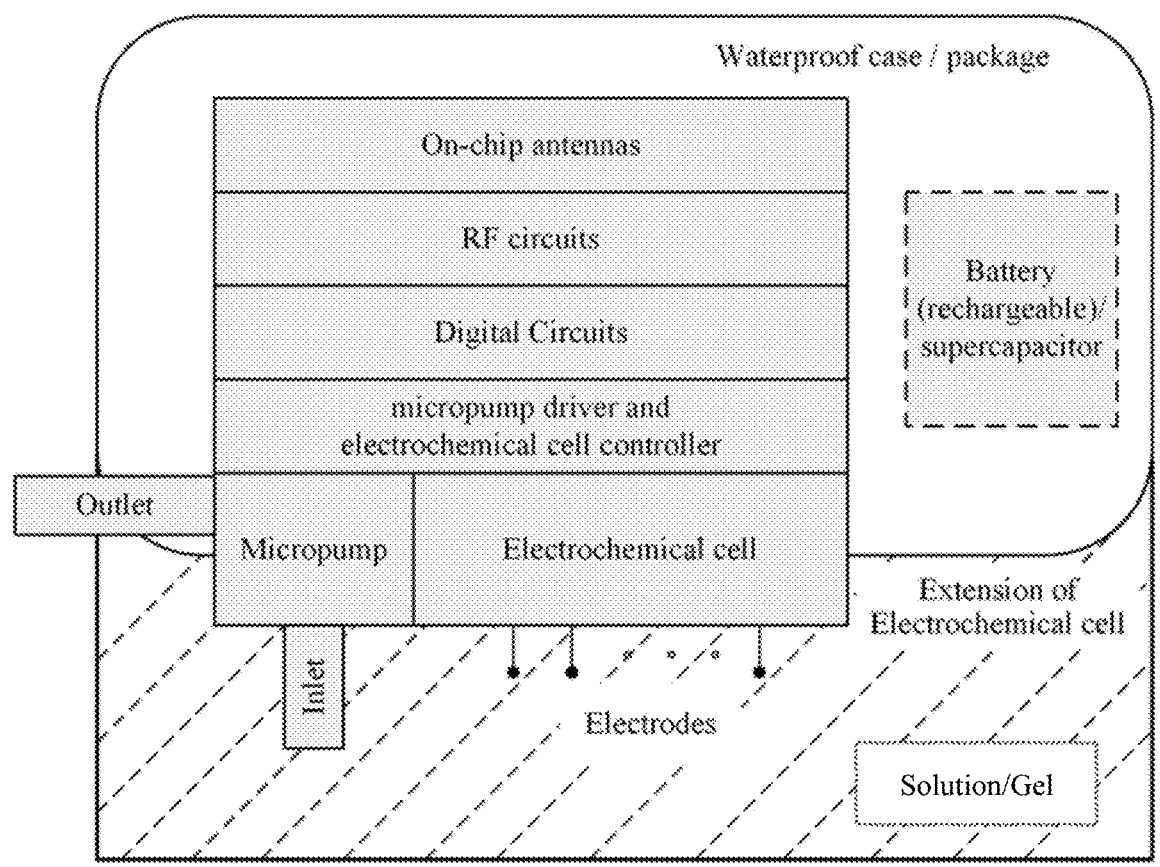
FIG. 2 is a block diagram of a wireless drug delivery integrated circuit (IC) according to an embodiment of the present invention.

FIG. 2 illustrates a wireless drug delivery system according to an embodiment of the present invention. Referring to FIG. 2, the system includes digital and RF circuits, on-chip antennas, a micropump, an inlet, an outlet, an electrochemical cell, a micropump driver and electrochemical cell controller, electrodes, a solution/gel, a waterproof case/package, and a battery/supercapacitor. As discussed herein, it is preferable to implement all the components on a single chip, but they can alternatively be stacked or attached to the circuit board. The electronics, wafer, and/or IC package can be surrounded by a waterproof case to protect it from the surrounding environment.

Figure 3:
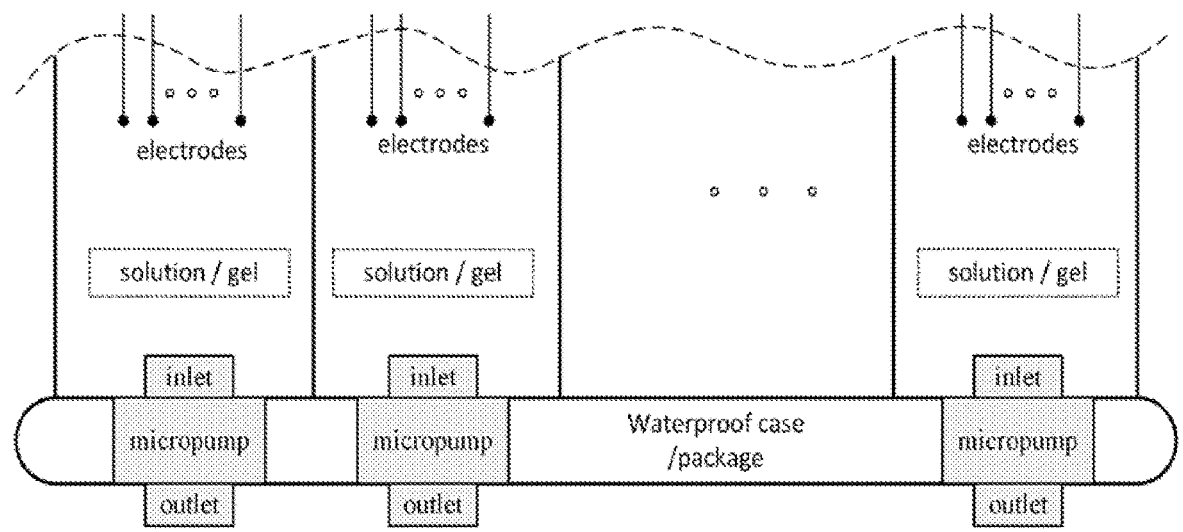
FIG. 3 is a block diagram of an embodiment of the present invention that has multiple gel/solution modules with separate micropumps.
Figure 4:
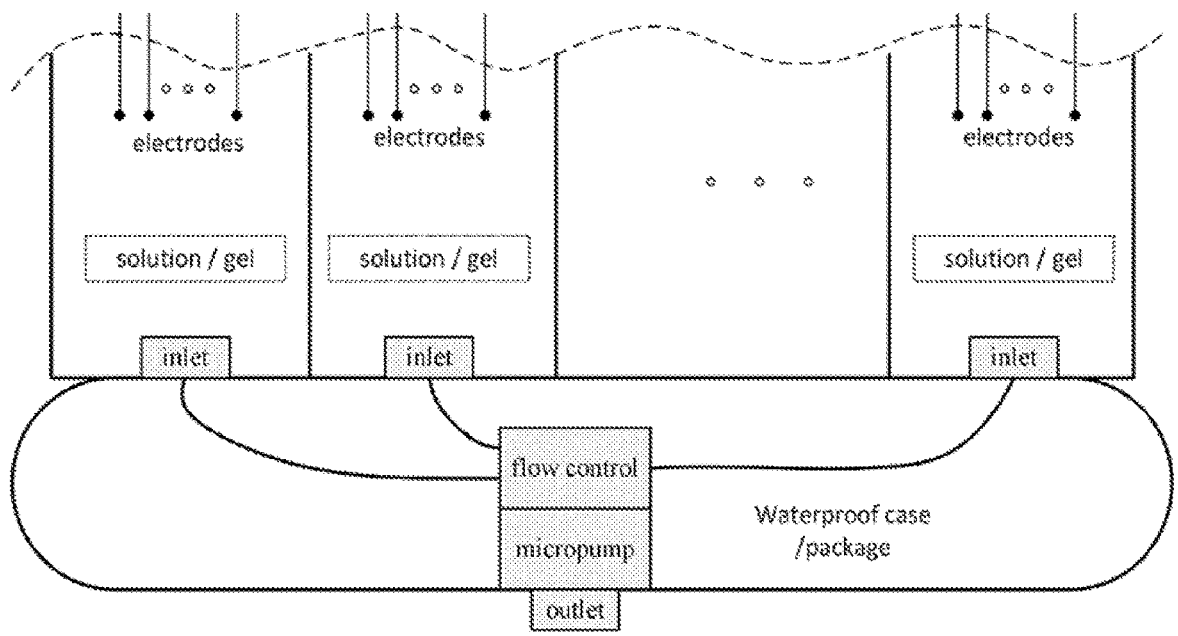
FIG. 4 is a block diagram of an embodiment of the present invention that has multiple gel/solution modules using one micropump and a flow controller.

As shown in FIGS. 2, 3, and 4, the electrochemical cell can have more electrodes than just a single anode and cathode. More than two electrodes can be used for failure redundancy and/or controlling the release of one drug using multiple potentials, or different electrodes can be coated with different drugs for individual controlled release. In addition, as illustrated in FIGS. 3 and 4, multiple different drugs or the same drug can be stored in different solution/gel compartments (or chambers), and their release can be controlled by different electrodes. For example, one, two, three, four, five, six or even more pairs of electrodes can release one, two, three, four, five, six or even more types of drugs. In another example, one, two, three, four, five, six or even more anodes can be used with one cathode (or vice versa, i.e., one, two, three, four, five, six or even more cathodes can be used with one anode). In addition, one, two, three, four or even more drugs can be combined on a single electrode. Examples of drugs that can be applied to the present invention include anions (e.g. ATP, dexamethasone, glutamate, salicylate, naproxen), cations (e.g. dopamine and chlorpromazine), and neutral compounds (e.g., nerve growth factor). If desired, micropumps can be added for further controlling drug release. Alternatively, instead of using electrodes, one, two, three, four, five, six or even more types of drugs can be administered solely using compartments containing drug solutions and be administered via one, two, three, four, five, six or even more micropumps. And, instead of using multiple micropumps, one micropump with a flow controller can be used for controlling the release of different drugs, as shown in FIG. 4. A mixing unit may also be provided in which drugs are mixed before being administered.

The electrodes can maintain a constant potential difference (e.g., 0.6 V for a period of time, such as 30 seconds, and then turn off), the potentials can change over time (e.g., increase from 0.2V -0.6V over a period of time, such as 30 seconds), or multiple different potentials can be enabled for different time periods (i.e., the voltage difference and time durations can be arbitrarily selected and are only limited by the hardware components). In further embodiments, the potential difference across the electrodes can be sinusoidal, saw-tooth, rectangular/square, and triangular waves as well as pulse width modulation. The wireless controller device can also monitor and send temperature data, humidity, blood analysis, sugar levels, and so forth. In biological applications, temperature data is an important factor to be considered as the temperature of a patient is indicative of their health and can influence the rate of drug release from a polymer-based drug delivery device.

Figure 5:
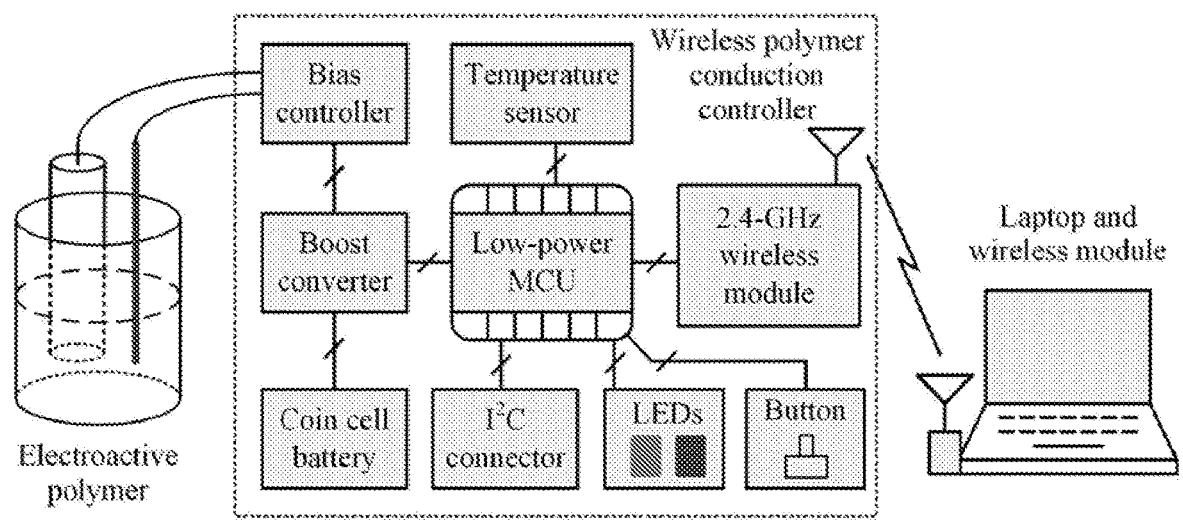
FIG. 5 is a simplified block diagram of an embodiment of the present invention.

FIG. 5 illustrates a wireless drug delivery integrated system according to an embodiment of the present invention that includes an electroactive polymer cell, a control module (laptop and wireless module), and wireless drug delivery integrated circuit (i.e., a WDDIC). An electrochemical cell is connected to the WDDIC. The WDDIC includes a bias controller, a boost converter, a coin cell battery, a temperature sensor, a lower-power MCU, LEDs, a button, an I2C connector, and a wireless module (e.g., a 2.4 GHz wireless module).

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A drug delivery system comprising:
a control module;
a wireless drug delivery integrated circuit;
a first electrode and a second electrode, which are both attached to the wireless drug delivery integrated circuit;
a first electroactive polymer; and
a first pharmaceutical compound.

Embodiment 2

The drug delivery system of embodiment 1, wherein the first electroactive polymer and the first pharmaceutical compound are layered as films on the first electrode.

Embodiment 3

The drug delivery system of any of embodiments 1-2, wherein the wireless drug delivery integrated circuit includes multiple antennas that are suitable for supplying energy to the wireless drug delivery integrated circuit.

Embodiment 4

The drug delivery system of any of embodiments 1-3, wherein the first electrode is comprised of a bioinert glassy carbon.

Embodiment 5

The drug delivery system of any of embodiments 1-4, wherein the second electrode is comprised of platinum.

Embodiment 6

The drug delivery system of any of embodiments 1-5, further comprising a third electrode and a fourth electrode in a second chamber with a second pharmaceutical compound, and wherein the first electrode and the second electrode are contained in a first chamber with the first pharmaceutical compound.

Embodiment 7

The drug delivery system of any of embodiments 1-6, further comprising an inlet, an outlet, a chamber, and a micropump.

Embodiment 8

The drug delivery system of any of embodiments 1-7, further comprising:
a first inlet, a first outlet, and a first micropump in the first chamber; and a second inlet, a second outlet, and a second micropump in the second chamber.

Embodiment 9

The drug delivery system of any of embodiments 1-7, further comprising a first inlet in the first chamber; a second inlet in the second chamber, a flow control connected to the first inlet and the second inlet, a micropump connected to the flow control, and an outlet connected to the micropump.

Embodiment 10

The drug delivery system of any of embodiments 1-9, wherein the control module includes a graphical user interface that displays a temperature received from the wireless drug delivery integrated circuit and is suitable for controlling the wireless drug delivery integrated circuit;
and wherein the graphical user interface includes options of voltage applied, voltage duration, initiation of the voltage applied, and stopping the voltage applied.

Embodiment 11

A drug delivery method comprising:
providing a wireless drug delivery integrated circuit;
providing a control module suitable for controlling the wireless drug delivery integrated circuit;
providing a first electrode and a second electrode, which are both attached to the wireless drug delivery integrated circuit;
providing a first electroactive polymer;
providing a first pharmaceutical compound;
releasing the first pharmaceutical compound into a first solution by generating a first voltage difference between the first electrode and the second electrode.

Embodiment 12

The method of embodiment 11, further comprising:
providing a third electrode and a fourth electrode and releasing a second pharmaceutical compound.

Embodiment 13

The method of any of embodiments 11-12, further comprising:
providing a first chamber that contains the first solution, the first electrode, and the second electrode;
providing a first inlet, a first micropump, and a first outlet, controlling a release of the first pharmaceutical compound out of the first chamber using the first inlet, the first micropump, and the first outlet.

Embodiment 14

The method of any of embodiments 11-13, wherein the first electroactive polymer comprises oligoanilines linked to polycaprolactone (PCL, 2 kDa) via ester bonds.

Embodiment 15

The method of any of embodiments 11-14, wherein the first electroactive polymer and the first pharmaceutical compound are layered in films on the first electrode.

Embodiment 16

A drug delivery system comprising:
a drug delivery integrated circuit;
a first electrode and a second electrode, which are both attached to the drug delivery integrated circuit;
a first electroactive polymer; and
a first pharmaceutical compound.

Embodiment 17

The drug delivery system of embodiment 16, wherein the first electroactive polymer and the first pharmaceutical compound are layered as films on the first electrode.

Embodiment 18

The drug delivery system of any of embodiments 16-17, wherein the first electrode is comprised of a bioinert glassy carbon.

Embodiment 19

The drug delivery system of any of embodiments 16-18, wherein the second electrode is comprised of steel, platinum, iridium oxide, gold, magnesium, tungsten, silicon, or platinum-iridium.

Embodiment 20

The drug delivery system of any of embodiments 16-19, further comprising a third electrode and a fourth electrode in a second chamber with a second pharmaceutical compound, and wherein the first electrode and the second electrode are contained in a first chamber with the first pharmaceutical compound.

Embodiment 21

The drug delivery system of any of embodiments 16-20, further comprising an inlet, an outlet, a chamber, and a micropump.

Embodiment 22

The drug delivery system of any of embodiments 16-21, further comprising:
a first inlet, a first outlet, and a first micropump in the first chamber; and a second inlet, a second outlet, and a second micropump in the second chamber.

Embodiment 23

The drug delivery system of any of embodiments 16-21, further comprising a first inlet in the first chamber; a second inlet in the second chamber, a flow control connected to the first inlet and the second inlet, a micropump connected to the flow control, and an outlet connected to the micropump.

Embodiment 24

The drug delivery system of any of embodiments 16-23, wherein a voltage is applied across the first electrode and the second electrode, and wherein the voltage threshold is triggered by a measurement threshold.

Embodiment 25

The drug delivery system of embodiment 24, wherein the measurement threshold is one or more of a timing sequence and a solution concentration.

Embodiment 26

The drug delivery system of embodiment 26, wherein the solution concentration is one or more of a sugar concentration, salt concentration, and hormone concentration.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 7:
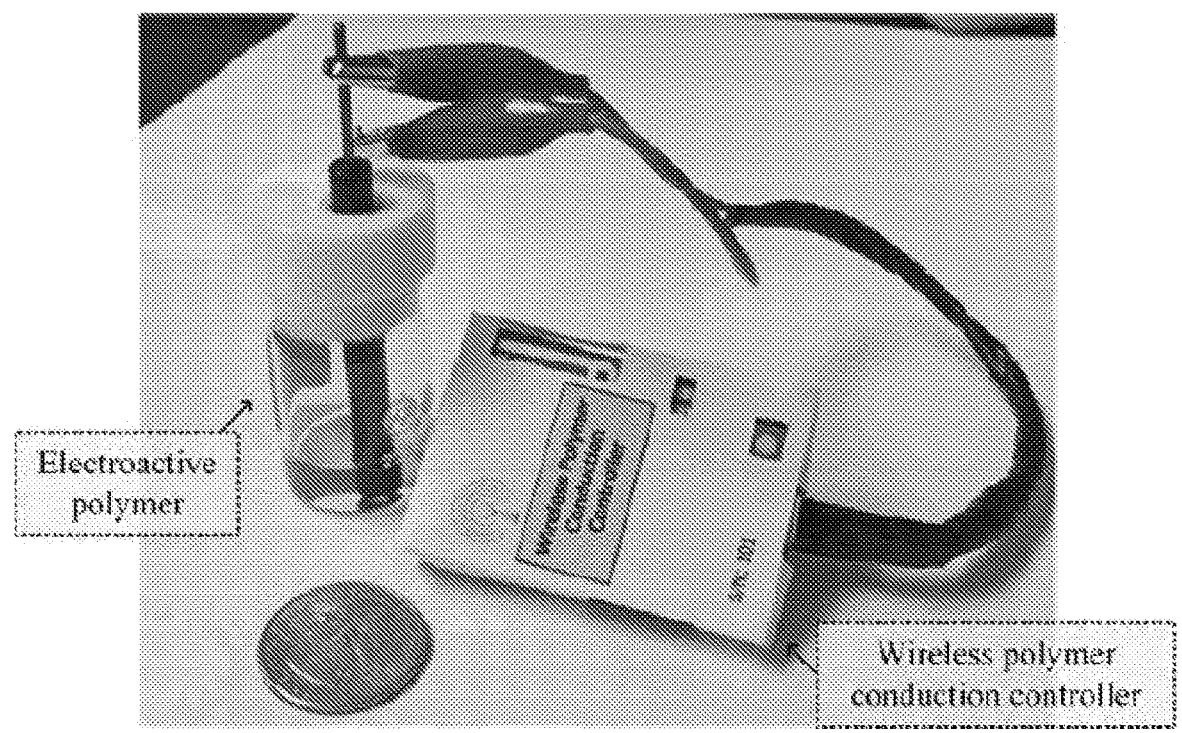
FIG. 7 shows an experimental test setup of a wireless drug delivery integrated circuit attached to an electrochemical cell with a U.S. quarter dollar coin for comparison.
Figure 8:
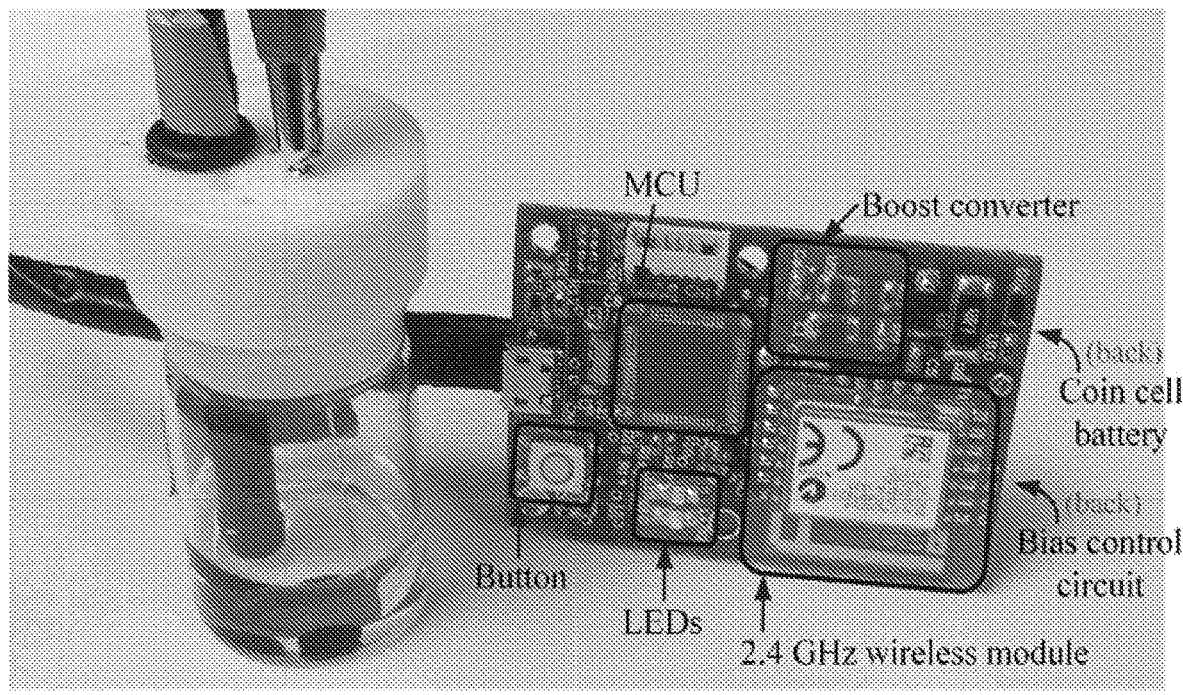
FIG. 8 is an image of an embodiment of a wireless drug delivery integrated circuit according to an embodiment of the present invention.

A wireless drug delivery integrated circuit (WDDIC) as shown in FIG. 7 was fabricated. Another image of this WDDIC can be seen with its cover removed in FIG. 8. The WDDIC included a low-power micro-controller (MCU), a 2.4-GHz wireless module, a bias controller, a temperature sensor, and a boost converter. The WDDIC was designed to be compact with the printed circuit board (PCB) having measurements close to that of a standard credit card (85.7× 54.0 mm, 3.375×2.125 in). The anode and cathode wires were attached to a bias controller block and clipped to a platinum electrode (a platinum wire) and a working electrode, which was made of bioinert glassy carbon and supported the polymer films. The platinum electrode and the working electrode were immersed in PBS (4 mL) and housed in a glass beaker with a fitted lid. The hardware was designed for low-power consumption. The firmware of the MCU controlled the MCU itself, the wireless module on the PCB, and the temperature sensor.

Active and sleep modes of the MCU were used to increase the length of the battery life. Power was provided by a coin cell battery that would last for two or three months under representative operating conditions. A Texas Instruments (TI) MSP430 MCU was used, in part because it supports several layers of active and sleep modes. An external 32.768 kHz crystal oscillator was placed on the board for an auxiliary clock, which enabled the use of deeper level of sleep modes by waking up the MCU using the auxiliary clock. An Advanced and adaptive Network Technology (ANT) wireless module was mounted on the board and connected to the MCU through a universal asynchronous receiver/transmitter (UART) interface. The ANT is an ultra-low power wireless protocol that can send wireless information from one device to another. The ANT supports many sensor network topologies, such as peer-to-peer, star, and practical mesh. The 2.4-GHz ANT module can use any RF frequency from 2.4 to 2.524 GHz, other than 2.457 GHz (reserved for ANT+). The MCU controls the ANT module during active or sleep modes. Effective use of the sleep modes of the ANT module makes it possible to further reduce power consumption.

Figure 9:
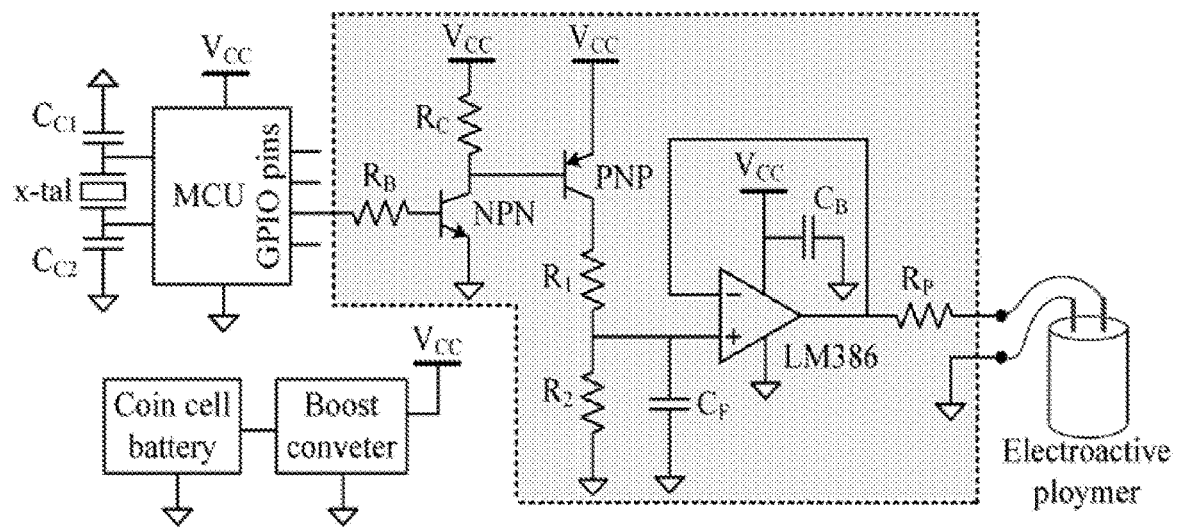
FIG. 9 is circuit diagram of the bias controller, power supply, and a part of the MCU of the embodiment shown in FIG. 8.

The bias controller block was designed and attached to the back of the main PCB. A circuit diagram of the bias controller is shown in FIG. 9. One of the general-purpose input/output (GPIO) pins was selected to control the applied voltage to the polymer films. The bias controller block included an operational amplifier (OP-AMP) buffer circuit. A LM386 OP-AMP was used as part of a buffer circuit. The input voltage of the buffer circuit was 0.6 V. The desired voltage can be obtained by the divided ratio of two resistors R1 and R2. One node of the resistor R1 is attached to the collector node of a PNP transistor. The emitter node of the PNP transistors is attached to a 3.3-V output voltage of the boost converter. The output of the buffer circuit was attached to the resistor(s) RP, which was used for protection. The anode and cathode electrodes of the polymer films were connected between the protection resistor RP and ground nodes. The collector nodes of NPN transistors were attached to the base of PNP transistor, and the current of the base of the NPN transistors was controlled by the voltage level of one of the GPIO pins through the resistor RB. For instance, if the level of the GPIO pin was high, there was 0.6 V difference between the anode and cathode nodes of the polymer films. When the level of the GPIO pin was low, there was approximately zero voltage across the anode and cathode nodes.

The microprocessor firmware was developed using mixed C and Assembly languages. The structure of the firmware program was a finite state machine. First, the controller device started operations with an initialization state. If the button was pressed in a turned-off state or a new battery was inserted, the firmware began initialization of the hardware. After the initialization state was finished, it went into a normal loop state. In the normal loop state, the device executed essential operations such as controlling the wireless module and temperature sensor and afterwards the controller device went into sleep mode. The controller device was designed to wake up every two seconds and resume the normal loop state when triggered by an internal wake up signal. For precise timing of drug release, the start time of the active bias control signal lagged to the closest second to synchronize with the MCU clock instead of immediate activation of the bias control signal. For safety, if an emergency stop event occurred, the bias control signal was immediately rendered inactive.

The wireless polymer conduction controller (control module) program was developed using Visual C++. As described herein, the ANT wireless protocol was used for communication. In the normal state of operation, the wireless polymer conduction controller sent a broadcast information packet every two seconds as the WDDIC woke up from the sleep mode. The information packet included temperature sensor data, the device ID, and status information. The controller program received the packet data and then stored and displayed the information.

Figure 10:
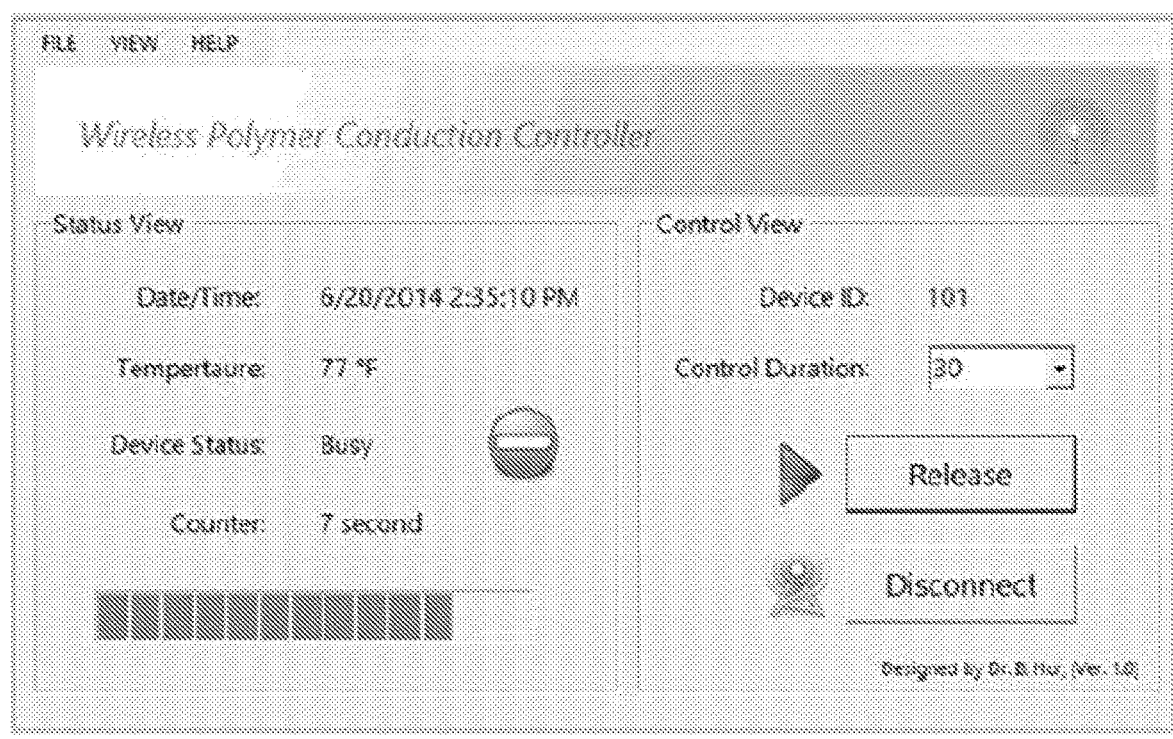
FIG. 10 is an image of the user interface of an embodiment of the control module of the present invention.

A graphical user interface (GUI) control program on a laptop computer (control module) managed communication with the WDDIC and received device information, device status, and temperature data. The user interface of the wireless polymer conduction controller program of this example is illustrated in FIG. 10. A 'Release' button was located on the right side. Above the "Release" button, there was a control duration drop down menu, which can select pre-determined periods such as 10, 20, and 30 seconds, or a user can manually type in the period. If the release button is clicked, the control program sends an event to the WDDIC. If the received event is valid, the wireless controller sets the bias control signal active for the given period of time. Afterwards, the controller sets the bias control back to being inactive. Once the drug release process starts, the counter begins counting backwards from the given time and the release button will not accept another click event until the counter reaches zero so that accidently performing unwanted operations is avoided. However, there is a stop button if the user wishes to cancel the ordered operation.

Example 2

Figure 11:
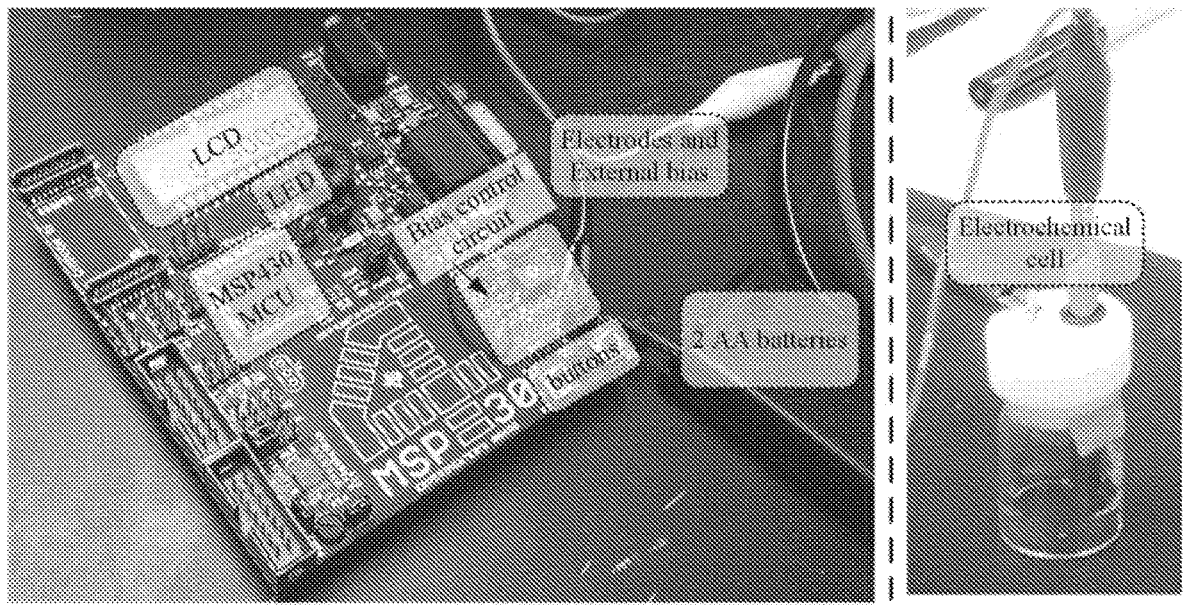
FIG. 11 is an image of an embodiment of a drug delivery integrated circuit of the present invention.

As shown in FIG. 11, a non-wireless drug delivery integrated circuit (DDIC) was constructed. A MSP430FG4618/F2013 experimenter board was used as the main controller. The custom bias control circuits were placed in the lower right corner of the experimenter board. Buttons and an LCD were used for selection of the pre-defined test durations and voltages, and the start and stop of the test sequences. The bias controller circuit used in this example, which did not include a LM386 buffer circuit, was a modified version of the circuits shown in FIG. 9. The collector voltages of the NPN and the PNP transistors were provided by an external power supply. Anti-inflammatory DMP was used as a clinically relevant model drug because it is straightforward to quantify its release using UV spectroscopy. However, a wide variety of other biologically-active molecules can be delivered using the methods described herein.

Example 3

The DDIC of Example 2 was tested. The purpose of this experimentation was to test the capability of the electroactive polymers to deliver DMP into a physiologically relevant electrolyte solution of phosphate buffered saline (PBS).

Figure 6:
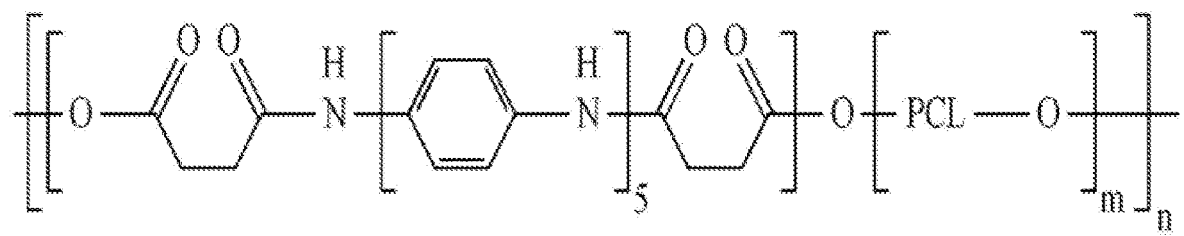
FIG. 6 illustrates the structure of electroactive polymers including oligoanilines linked to polycaprolactone (PCL, 2 kDa) via ester bonds.

Electroactive polymers were used to deliver dexamethasone phosphate (DMP). The electroactive polymers consisted of blocks of electroactive oligoanilines linked to non-electroactive polycaprolactone (PCL, 2 kDa) via ester bonds and were prepared as described in Hardy et al. ("Biodegradable' electroactive polymers for electrochemically-triggered drug delivery," 2014), which is incorporated by reference herein in its entirety. The structure of this type of biodegradable electroactive polyester film is shown in FIG. 6. A stock solution of the polymer and DMP (90 mg polymer, 10 mg DMP, 500 µl hexafluoroisopropanol) was formed, and films of approximately 5 mg (as determined using a high precision balance) were cast on bioinert glassy carbon working electrodes and dried under high vacuum.

A constant electrical stimulation of 0.6V was applied for 30 seconds, followed by a relaxation time of 9.5 minutes (i.e., for a total of 10 minutes). Then, the concentration of DMP was determined using UV-visible spectroscopy. The films were stimulated again for 30 seconds and allowed to rest for another 9.5 minutes (i.e., for a total of 20 minutes), after which the concentration of DMP was again determined. The films were then stimulated a third time for 30 seconds and again allowed to rest for 9.5 minutes (i.e., for a total of 30 minutes), after which the concentration of DMP was finally measured. PBS is ideal for measurement of DMP release by UV-visible spectroscopy, wherein the absorption of DMP is measured at 242 nm (its absorption maximum). DMP release was quantified by UV spectroscopy in accordance with the methodology of Gao et al. ("Action at a distance: Functional drug delivery using electromagnetic-field-responsive polypyrrole nanowires," 2014), which is incorporated by reference herein in its entirety. Measurements employed a BioTek Epoch® plate reader (BioTek US, Winooski, Vt.) equipped with a Take3 Micro-volume Plate and Gen5 v2.04 Software supplied with the plate reader.

Figure 12:
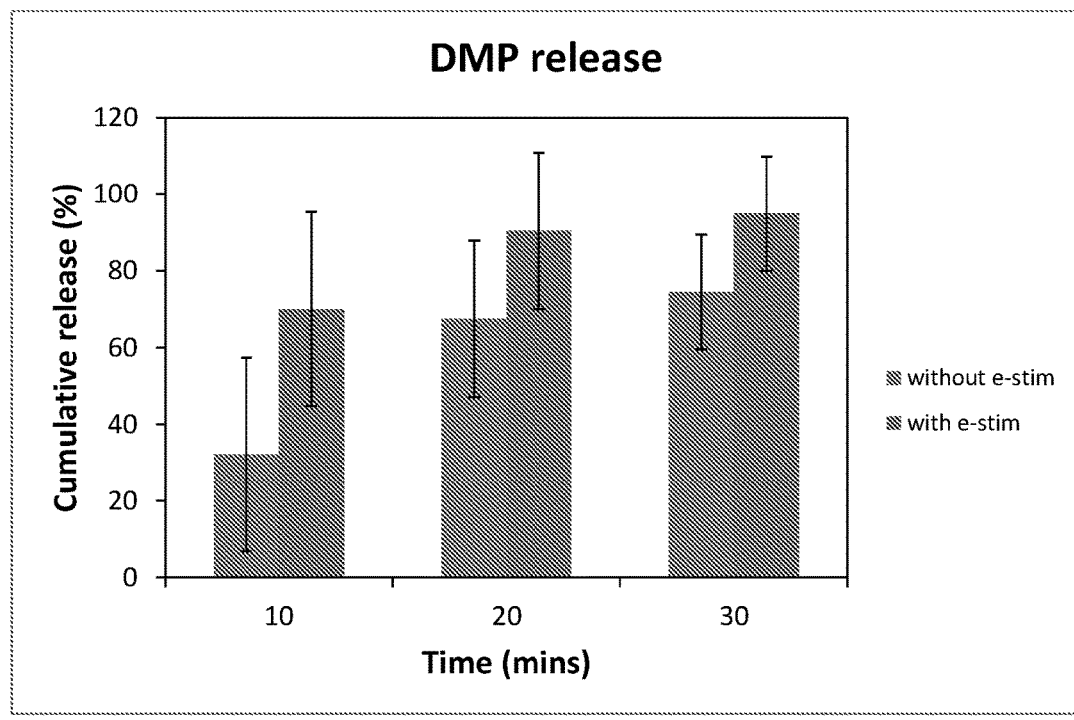
FIG. 12 is a graph illustrating the percentage of dexamethasone phosphate (DMP) released from films of biodegradable electroactive polymers over time, with and without electrical stimulation.

FIG. 12 shows the results of the DMP release experiments with electrical stimulation, and without electrical stimulation (i.e., leaching of the drug from the polymer matrix because the films swell when immersed in PBS). It was observed that more DMP had leached out after an additional 20 minutes (30 minutes total time since immersion in PBS). A second period of electrical stimulation enhanced the release of DMP relative to the unstimulated films. The error bars represent standard deviations (n=5).

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

What is claimed is:

1. A drug delivery system, comprising:
   a control module;
   a wireless drug delivery integrated circuit;
   a first electrode and a second electrode, wherein the first electrode and the second electrode are both attached to the wireless drug delivery integrated circuit;
   a first electroactive polymer; and
   a first pharmaceutical compound, wherein the first pharmaceutical compound is released into a first solution in a chamber in response to a first voltage difference applied between the first electrode and the second electrode.

2. The drug delivery system according to claim 1, wherein the first electroactive polymer and the first pharmaceutical compound are layered as films on the first electrode.

3. The drug delivery system according to claim 1, wherein the wireless drug delivery integrated circuit includes multiple antennas configured to supply energy to the wireless drug delivery integrated circuit.

4. The drug delivery system according to claim 1, wherein the first electrode comprises a bioinert glassy carbon, and wherein the second electrode comprises platinum.

5. The drug delivery system according to claim 1,
wherein the control module includes a graphical user interface that displays a temperature received from the wireless drug delivery integrated circuit and is configured to control the wireless drug delivery integrated circuit, and
wherein the graphical user interface includes options of voltage applied, voltage duration, initiation of the voltage applied, and stopping the voltage applied.

6. The drug delivery system according to claim 1, wherein the first electrode and the second electrode are contained in a first chamber with the first pharmaceutical compound, and wherein the drug delivery system further comprises a third electrode and a fourth electrode in a second chamber with a second pharmaceutical compound.

7. The drug delivery system according to claim 6, further comprising:
a first inlet, a first outlet, and a first micropump in the first chamber; and
a second inlet, a second outlet, and a second micropump in the second chamber.

8. The drug delivery system according to claim 6, further comprising:
a first inlet in the first chamber;
a second inlet in the second chamber;
a flow control connected to the first inlet and the second inlet;
a micropump connected to the flow control; and
an outlet connected to the micropump.

9. A drug delivery method, comprising:
providing a wireless drug delivery integrated circuit;
providing a control module suitable for controlling the wireless drug delivery integrated circuit;
providing a first electrode and a second electrode, which are both attached to the wireless drug delivery integrated circuit;
providing a first electroactive polymer;
providing a first pharmaceutical compound;
releasing the first pharmaceutical compound into a first solution in a chamber by generating a first voltage difference between the first electrode and the second electrode.

10. The method according to claim 9, further comprising:
providing a third electrode and a fourth electrode and releasing a second pharmaceutical compound.

11. The method according to claim 9, further comprising:
providing a first chamber that contains the first solution, the first electrode, and the second electrode;
providing a first inlet, a first micropump, and a first outlet; and
controlling a release of the first pharmaceutical compound out of the first chamber using the first inlet, the first micropump and the first outlet.

12. The method according to claim 9, wherein the first electroactive polymer and the first pharmaceutical compound are layered in films on the first electrode.

13. The method according to claim 9, wherein the first electroactive polymer comprises oligoanilines linked to polycaprolactone (PCL) via ester bonds.

14. A drug delivery system, comprising:
a drug delivery integrated circuit;
a first electrode and a second electrode, which are both attached to the drug delivery integrated circuit;
a first electroactive polymer; and
a first pharmaceutical compound, wherein the first electroactive polymer and the first pharmaceutical compound are layered as films on the first electrode;
wherein a voltage is applied across the first electrode and the second electrode,
wherein a voltage threshold is triggered by a measurement threshold, and
wherein the measurement threshold is at least one of a timing sequence and a solution concentration, where the solution concentration is at least one of a sugar concentration, a salt concentration, and a hormone concentration.

15. The drug delivery system according to claim 14, wherein the first electrode comprises a bioinert glassy carbon, and
wherein the second electrode comprises at least one of steel, platinum, iridium oxide, gold, magnesium, tungsten, silicon, and platinum-iridium.

16. The drug delivery system according to claim 14, wherein the first electrode and the second electrode are contained in a first chamber with the first pharmaceutical compound, and
wherein the drug delivery system further comprises a third electrode and a fourth electrode in a second chamber with a second pharmaceutical compound.

17. The drug delivery system according to claim 16, further comprising:
a first inlet, a first outlet, and a first micropump in the first chamber; and
a second inlet, a second outlet, and a second micropump in the second chamber.

18. The drug delivery system according to claim 16, further comprising:
a first inlet in the first chamber;
a second inlet in the second chamber;
a flow control connected to the first inlet and the second inlet;
a micropump connected to the flow control;
and an outlet connected to the micropump.

* * * * *